United States Patent [19]
Van Tassel et al.

[11] Patent Number: 5,292,309
[45] Date of Patent: Mar. 8, 1994

[54] SURGICAL DEPTH MEASURING INSTRUMENT AND METHOD

[75] Inventors: Robert A. Van Tassel, Excelsior, Minn.; Joshua Makower, Nanuet, N.Y.; Robert J. Thatcher, Eden Prairie, Minn.

[73] Assignee: Schneider (USA) Inc., Plymouth, Minn.

[21] Appl. No.: 7,696

[22] Filed: Jan. 22, 1993

[51] Int. Cl.$^5$ ............................................. A61M 5/00
[52] U.S. Cl. .................................... 604/117; 604/116
[58] Field of Search ......................... 604/117, 159, 116

[56] References Cited

U.S. PATENT DOCUMENTS

| | | |
|---|---|---|
| 4,235,234 | 11/1980 | Whitney et al. ................. 604/117 |
| 4,299,230 | 11/1981 | Kubota .............................. 604/117 |
| 4,356,822 | 11/1982 | Winstead et al. ................. 604/117 |
| 4,645,491 | 1/1987 | Evans . |
| 4,649,915 | 3/1987 | Heyden . |
| 4,662,870 | 5/1987 | Augustine et al. . |
| 4,690,138 | 9/1987 | Heyden . |
| 4,710,171 | 12/1987 | Rosenberg . |
| 4,710,173 | 12/1987 | McFarlane . |
| 4,760,847 | 8/1988 | Vaillancourt . |
| 4,767,408 | 8/1988 | McFarlane . |
| 4,772,264 | 9/1988 | Cragg . |
| 5,069,665 | 12/1991 | Ng .................................... 604/117 |
| 5,084,022 | 1/1992 | Claude . |
| 5,106,376 | 4/1992 | Mononen et al. . |
| 5,147,315 | 9/1992 | Weber . |

Primary Examiner—Paul J. Hirsch
Attorney, Agent, or Firm—Haugen and Nikolai

[57] ABSTRACT

A device for measuring the depth below skin level of a blood vessel that has been punctured in the course of a catheterization or other interventional vascular procedure comprises a tubular member having a proximal end and a distal end portion that is preferably tapered to a small outer diameter. The lumen may have a stepped diameter extending between the proximal and distal ends. A first portion of the lumen is distally located and is of a diameter generally equal to the diameter of a guidewire with which the measuring device is used. The second segment of the lumen is of a substantially larger diameter. A side entry port is made through the wall of the tubular member at the distal base of the larger diameter section of the lumen. Graduated markings on the side wall of the tubular member extend from the side entry port toward the proximal end of the instrument. When the instrument is fed over a guidewire into a puncture wound formed through the skin and into an artery, the wall of the artery can be accurately located relative to the skin's surface by noting the graduated markings on the exterior of the tube at the point where blood flow enters the side entry port and fills the larger diameter lumen. Rather than having two coaxially disposed lumens as above, the tubular member may have a double lumen, one extending the entire length for accommodating the guidewire and the other extending between the tube's proximal end and the side entry port.

10 Claims, 1 Drawing Sheet

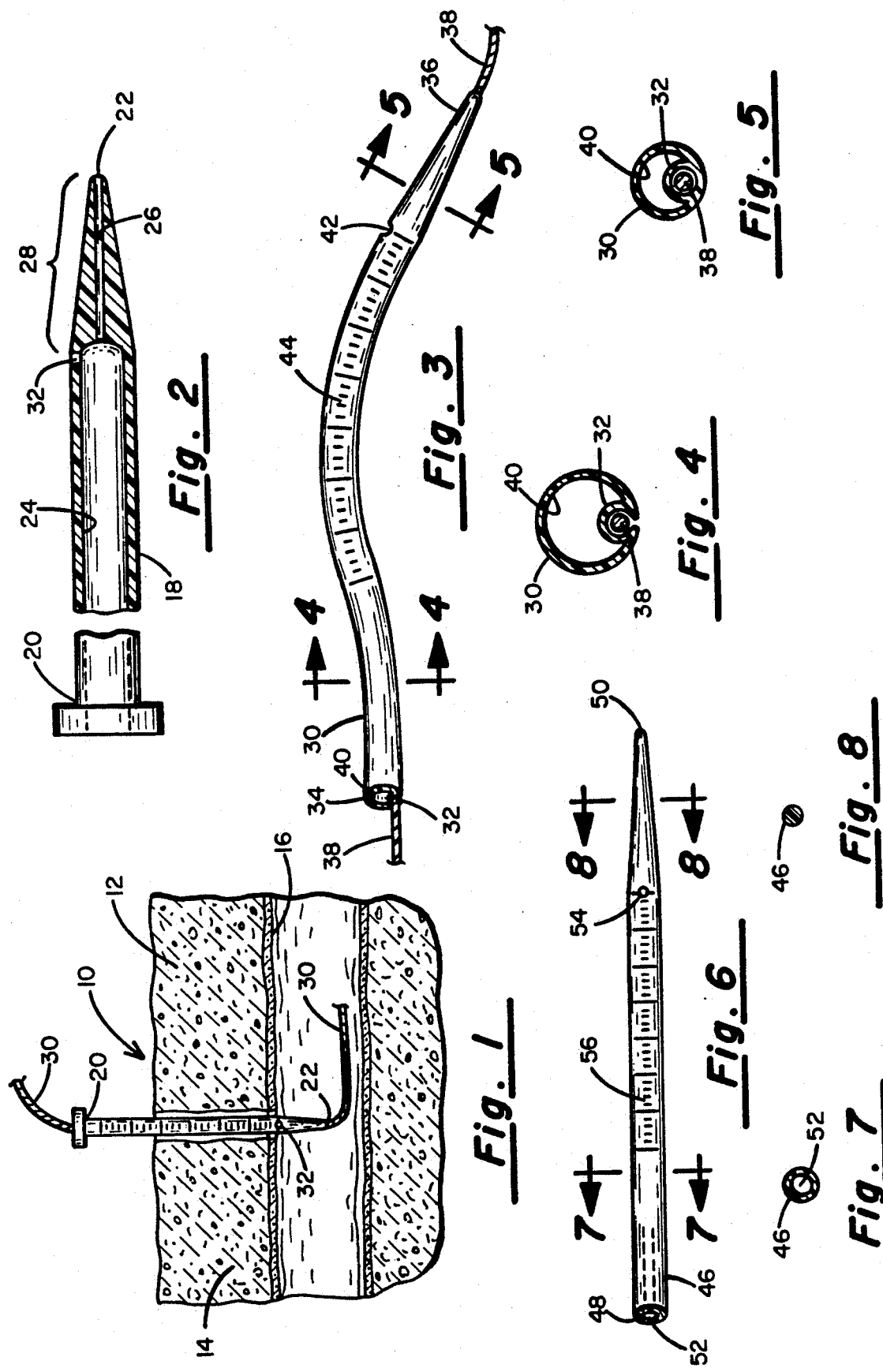

SURGICAL DEPTH MEASURING INSTRUMENT AND METHOD

BACKGROUND OF THE INVENTION

I. Field of the Invention

This invention relates generally to a surgical instrument used during a vascular interventional procedure, and more particularly to an instrument for accurately measuring the depth below the skin surface of the blood vessel through which the vascular catheter is to be passed.

II. Discussion of the Prior Art

In a typical interventional procedure, such as the placement of a vascular catheter, the so-called Seldinger procedure is used to gain access to a blood vessel. More particularly, a needle trocar is passed through the skin to puncture an opening through the wall of an artery. Next, a dilator may be passed over the trocar to slightly enlarge the diameter of the puncture wound so that it can accommodate a tubular introducer. Once the introducer is in place, an elongated, flexible guidewire may be passed through the introducer into the blood vessel. An interventional device may then be advanced over the guidewire and through the vascular system.

Once the procedure in question has been concluded and the interventional device has been withdrawn, any guide catheter, the guidewire and the introducer must also be removed. As is explained in a co-pending U.S. Pat. application of Makower et. al. Ser. No. 07/912,921, filed Jul. 13, 1992, and entitled "HEMOSTATIC IMPLANT INTRODUCER", a difficulty often arises in stemming the flow of blood through the entry wound. When only manual pressure is relied upon to stem the blood flow, considerable time is required on the part of surgical personnel to maintain the pressure until clotting has taken place. The device described in the aforereferenced Makower et. al. application has been especially designed to more rapidly effect hemostasis by providing a means for injecting a mass of hemostatic material (collagen) as a plug into the puncture wound. That device is intended to position the collagen plug beneath the skin and directly in contact with the exterior wall of the punctured blood vessel, but without introducing any of the collagen plug material through that puncture site. To accomplish this end, it is important that the depth of the punctured blood vessel beneath the skin surface be accurately gauged so that the surgeon can accurately place the barrel of the puncture sealing device (PSD) into the wound only to that desired depth, thus assuring that the plug will not be made to enter the blood vessel where it could act as a thrombogenic site.

SUMMARY OF THE INVENTION

It is accordingly a principal object of the present invention to provide a measuring instrument or gauge for accurately assessing the depth below the skin surface of a punctured blood vessel to be sealed.

In accordance with one embodiment of the invention, the gauge may comprise a plastic tubular member having a proximal end, a distal end, a lumen extending therebetween. Its outside diameter may taper to a somewhat rounded point at the distal end to facilitate its insertion into a previously formed puncture. The lumen is preferably of a reduced diameter proximate the distal end. It is of a size that receives a guidewire therethrough with only a slight clearance. A short predetermined distance proximal of the distal end segment the lumen is of a larger diameter. The larger lumen segment of the tubular member is in fluid communication with a side entry port formed through the wall of the tubular member at a location which is a short predetermined distance proximal of the distal end of the device. Provided along the outer wall surface of the device are suitable markings, such as graduations, colored bands, etc., extending proximally from the side entry port which can be used to reference the location of the side entry port relative to the skin surface. In use, the measuring device is passed over the proximal end of the guidewire and inserted into the puncture wound formed through the skin, into the blood vessel, and slowly advanced until blood is first seen to flow freely through the larger lumen segment of the measuring device and the proximal end. This reflects the fact that the side entry port has just entered the punctured blood vessel. The physician may then view the graduated markings on the exterior barrel of the instrument and note from the markings relative to the skin's surface the depth of the side entry port where blood flow through the lumen is first noted.

Because the device subsequently used to inject the hemostatic mass has corresponding markings on its exterior barrel surface, that puncture sealing device can be inserted to the same depth as earlier noted on the gauge of the present invention, thus insuring that its depth will ultimately position the hemostatic mass against the exterior wall of the blood vessel and not into it.

In accordance with an alternative embodiment, the tubular measuring device may have a lumen that does not extend completely to the distal end but only form the proximal end to the side entry port located a predetermined distance proximal of the distal end. The alternative device is used in much the same manner but without the use of a guidewire.

DESCRIPTION OF THE DRAWINGS

The foregoing features, objects and advantages of the invention will become apparent to those skilled in the art from the following detailed description of a preferred embodiment thereof, especially when considered in conjunction with the accompanying drawings in which like numerals in the several views refer to corresponding parts.

FIG. 1 is a plan view of the surgical depth measuring instrument comprising a preferred embodiment of the present invention;

FIG. 2 is an enlarged longitudinal cross-sectional view of the instrument of FIG. 1;

FIG. 3 is a side elevation of an alternative embodiment of the present invention;

FIG. 4 is a cross-sectional view taken along the line 4—4 in FIG. 3;

FIG. 5 is a cross-sectional view taken along the line 5—5 in FIG. 3;

FIG. 6 is a side elevation of another alternative embodiment;

FIG. 7 is a cross-sectional view taken along the line 7—7 in FIG. 6; and

FIG. 8 is a cross-sectional view taken along the line 8—8 in FIG. 6.

DESCRIPTION OF THE PREFERRED EMBODIMENT

With reference to FIG. 1, there is indicated generally by numeral 10 a first embodiment of the depth measuring instrument of the present invention. It is illustrated in greatly enlarged form as being disposed within a puncture wound formed through the skin 12 and the subcutaneous adipose tissue 14, with the distal end portion of the instrument entering a blood vessel, such as artery 16. The instrument itself is seen to comprise a rigid tubular member 18, preferably formed from a transparent plastic material and having a proximal end 20 and a distal end 22. As is apparent in the cross-sectional view of FIG. 2, the device includes first and second lumens 24 and 26 that together run the full length of the instrument. The distal end or tip 22 is slightly rounded to render it more atraumatic. Also, the distal end portion of the instrument is tapered over a zone identified by bracket 28 to facilitate its passage through the puncture wound previously formed through the skin layer 12 and the wall of the blood vessel 16.

The lumen 26 extending longitudinally through the zone 28 is of a diameter approximately equal to the outside diameter of a guidewire 30 with which the measuring instrument of the present invention may conveniently be used. The guidewire thus blocks the flow of blood through the distal end opening. The lumen 24, however, is of substantially larger diameter than the diameter of the guidewire 30 so that it will fit loosely within the lumen 24.

With continued reference to FIG. 2, numeral 32 identifies a side entry port which extends through the wall of the instrument at a predetermined location proximal of the distal end 22 of the instrument. The port 22 is drilled or otherwise formed to be proximate the junction between the larger lumen 24 and the smaller lumen 26.

FIG. 1 shows that the outer surface of the tubular member is scribed or embossed otherwise provided with graduated markings with the zero point at the location of the side port 32. Rather than using scale-like markings, colored bands may be utilized.

In use, and in accordance with the Seldinger technique, after the guidewire 30 is inserted through a trocar so that its distal end is within the lumen of the artery 16, the measuring instrument 10 of the present invention may be fed over the guidewire and advanced through the skin layer 12. Because the O.D. of the guidewire 30 is approximately equal to the diameter of the bore or lumen 26, it serves to block blood flow through that lumen as the distal tip 22 is made to enter through the puncture wound in the artery wall 16. However, as the instrument 10 is slowly advanced further into the wound, a point is reached where the side entry port 32 passes through the artery wall. Because the site of the side entry port is at the base of the larger diameter lumen 24, it will not be blocked by the presence of the guidewire and blood will flow through the side entry port to fill the larger diameter lumen 24. At the location where the surgeon first notices blood rising up the instrument to its open proximal end, he may note the graduated marking on the exterior of the barrel at the level of the skin surface. This provides an accurate measurement of the distance below the skin surface of the opening formed in the artery wall. Once the measurement has been taken, the instrument 10 may be removed from the guidewire and the interventional procedure can be carried out.

At the conclusion of the interventional procedure, the puncture sealing device described in the aforereferenced Makower et. al. application may be assembled onto the guidewire and advanced therealong until the distal tip of that instrument is at a depth below the skin surface corresponding to the measurement that had been earlier taken using the instrument of the present invention. The hemostatic plug can then be ejected from the PSD so as to reside in the puncture wound at a location abutting the exterior blood vessel wall 16.

ALTERNATIVE EMBODIMENTS

In accordance with a first alternative embodiment which is particularly illustrated in FIG. 3 and the cross-sectional views of FIGS. 4 and 5, the measuring instrument or gauge comprises an elongated flexible plastic tubular member 30 which may be formed from silicon rubber or other suitable material and which has a first lumen 32 extending the entire length thereof from its proximal end 34 to its distal end 36. The diameter of this first lumen is sufficiently large so that it can receive a guidewire 38 of a predetermined lesser diameter therethrough where that guidewire 38 effective occludes blood flow through the lumen 32. The flexible tubular member 30 has a second lumen 40 extending from the proximal end 34 thereof to a side entry port 42 located a predetermined distance proximal of the distal end 36 of the device. The guidewire lumen is preferably located so as to be tangent to the O.D. of the tube 30 as shown to provide as large an opening for the lumen 40 as can practically realized.

Again, graduated markings 44 are formed on the exterior wall surface of the tubular member 30 with the zero point disposed adjacent the side entry port 42 and extending in the proximal direction therefrom.

As in the case of the first embodiment, after the guidewire 38 is made to enter the blood vessel, the measuring instrument shown in FIG. 3 may be advanced over vessel. As the measuring instrument is further advanced along the guidewire, the point is reached where the physician will note the flow of blood out from the lumen 40, thus indicating that the side entry port 42 has entered the blood vessel in question. Now, by slowly drawing back the measuring instrument of the present invention in the distal direction until blood flow from the proximal end of the lumen 40 ceases, an accurate reading can be taken from the graduated markings of the depth below skin level of the side entry port 42 as it leaves the blood vessel. Again, this information can then be used when subsequently inserting the puncturing sealing device. In this way, the surgeon will know how deep to insert that device before releasing the hemostatic plug so that the hemostatic plug will reside against the exterior wall of the blood vessel in question.

Referring FIGS. 6-8, there is shown a second alternative embodiment of the invention. Again, the instrument comprises a tubular body 46 preferably formed of either a highly flexible or fairly rigid plastic material and having a proximal end 48 and a distal end 50. To aid in inserting the instrument of FIG. 6 into a puncture wound, it is preferable that the distal end portion thereof be tapered to a generally rounded, atraumatic tip. A lumen 52 extends from the proximal end 48 only to a side entry port 54 which is located a predetermined distance proximal of the distal end 50 of the instrument.

Etched or otherwise formed on the exterior surface of the tubular body 46 are graduated markings 56 which extend in the proximal direction from the side entry port 54. As is evident from the cross-sectional views of FIGS. 7 and 8, the lumen 52 need only extend to the side entry port and does not extend beyond it to the distal end 50.

The instrument illustrated in FIG. 6 would find application in situations where no guidewire is involved. The physician merely inserts the instrument into the already created puncture wound and advances the instrument until blood entering the side entry port 54 travels up the lumen 52 to exit at the proximal end 48. At the point at which the blood flow is detected, the physician may note using the scale 45 the distance below skin level of the side entry port.

This invention has been described herein in considerable detail in order to comply with the Patent Statutes and to provide those skilled in the art with the information needed to apply the novel principles and to construct and use such specialized components as are required. However, it is to be understood that the invention can be carried out by specifically different equipment and devices, and that various modifications, both as to the equipment details and operating procedures, can be accomplished without departing from the scope of the invention itself.

What is claimed is:

1. A device for measuring the depth below skin level of a blood vessel that has been punctured in the course of an interventional vascular procedure comprising:
   (a) a tubular member having a proximal end, a longitudinally tapered distal end portion terminating in a generally pointed tip and a wall defining a first lumen, said first lumen extending between said proximal end toward but short of said pointed tip;
   (b) a side entry port extending through said wall in fluid communication with said first lumen; and
   (c) graduated markings on said wall of said tubular member extending from said side entry port toward said proximal end of said tubular member.

2. A device for measuring the depth below skin level of a blood vessel that has been punctured in the course of an interventional vascular procedure and made to receive a guidewire therethrough comprising:
   (a) a tubular member having a proximal end, a distal end and a wall defining first and second lumens, said first lumen extending between said proximal end and said distal end and comprising a first diameter bore generally equal to the diameter of said guidewire, and second said lumen extending from said proximal end toward but short of said distal end;
   (b) a side entry port extending through said wall in fluid communication with said second lumen; and
   (c) graduated markings on said wall of said tubular member extending from said side entry port toward said proximal end of said tubular member.

3. The device as in claim 2 wherein said first and second lumens extend parallel to one another.

4. The device as in claim 3 wherein said first lumen in tangent to said wall.

5. The device as in claim 2 wherein said first and second lumens are concentric with one another, said second lumen having a diameter larger than that of said first lumen.

6. A device for measuring the depth below skin level of a blood vessel that has been punctured in the course of an interventional vascular procedure and made to receive a guidewire therethrough comprising:
   (a) a rigid tubular member having a proximal end, a distal end and a wall defining a lumen that extends between said proximal end and said distal end, the diameter of the lumen in a predetermined distal end zone being of a size generally equal to the diameter of said guidewire and the diameter of said lumen in a section of said tubular member proximal to said predetermined distal end zone being larger than the diameter of said guidewire, such that said guidewire will substantially totally occlude said lumen in said predetermined distal end zone and not in said proximal section;
   (b) a side entry port extending through said wall proximate the juncture of said predetermined zone with said proximal section; and
   (c) graduated markings on said wall of said tubular member extending from said port toward said proximal end.

7. A device for measuring the depth below skin level of a blood vessel that has been punctured in the course of an interventional vascular procedure and made to receive a guidewire therethrough comprising:
   (a) an elongated, flexible plastic tubular
   member having a wall surrounding a first lumen extending the full length thereof from a proximal end to a distal end of said tubular member and of a size to receive said guidewire therethrough with said guidewire substantially occluding said first lumen;
   (b) a second lumen formed in said tubular member extending parallel to said first lumen from said proximal end toward but short of said distal end;
   (c) a side entry port extending through said wall and in fluid communication with said second lumen; and
   (d) graduated markings formed on said wall extending from said side entry port toward said proximal end.

8. The device as in claim 7 wherein said wall is tapered to a lesser outer diameter in a zone of a predetermined length proximal of said pointed tip.

9. A method for measuring the depth below skin level of a blood vessel that has been punctured in the course of an interventional vascular procedure comprising the steps of:
   (a) inserting a guidewire through the puncture into said blood vessel;
   (b) passing over said guidewire a tubular member having a proximal end, a distal end and a wall defining a first lumen that extends between said proximal end and said distal end, the diameter of at least a portion of said first lumen being of a size generally equal to the diameter of said guidewire, a second lumen extending toward but short of said distal end, and said tubular member having a side entry port extending through said wall to intersect said second lumen and graduated markings on said wall of said tubular member extending from said port towards said proximal end;
   (c) advancing said tubular member until said side entry port enters through said puncture in said blood vessel as indicated by the flow of blood through said side entry port and the second lumen; and
   (d) using said graduated markings for noting the skin-level position relative to said side entry port at the point where blood flow is noted.

10. A method for measuring the depth below skin level of a blood vessel that has been punctured in the course of an interventional vascular procedure comprising the steps of:

(a) inserting a guidewire through the puncture into said blood vessel;

(b) passing over said guidewire a tubular member having a proximal end, a distal end and a wall defining a first lumen that extends between said proximal end and said distal end, the diameter of at least a portion of said first lumen being of a size generally equal to the diameter of said guidewire, a second lumen extending toward but short of said distal end, and said tubular member having a side entry port extending through said wall to intersect said second lumen and graduated markings on said wall of said tubular member extending from said port towards said proximal end;

(c) advancing said tubular member until said side entry port enters through said puncture in said blood vessel as indicated by the flow of blood through said side entry port and the second lumen;

(d) slowly withdrawing said tubular member until a cessation of blood flow in said second lumen is noted; and (e) using said graduated markings for noting the skin-level position relative to said side entry port at the point where cessation blood flow is noted.

* * * * *